United States Patent [19]

Gross et al.

[11] Patent Number: 5,082,632
[45] Date of Patent: Jan. 21, 1992

[54] REACTION VESSEL

[75] Inventors: Jürgen Gross, Hofheim am Taunus; Hugo Wilmes, Liederbach, both of Fed. Rep. of Germany

[73] Assignee: Hoechst Aktiengesellschaft, Frankfurt am Main, Fed. Rep. of Germany

[21] Appl. No.: 126,734

[22] Filed: Nov. 30, 1987

[30] Foreign Application Priority Data

Dec. 2, 1986 [DE] Fed. Rep. of Germany ....... 3641093

[51] Int. Cl.$^5$ ............................................. G01N 21/03
[52] U.S. Cl. ...................................... 422/102; 422/58; 422/99; 436/525; 436/165; 366/117
[58] Field of Search .................. 422/102, 58, 99, 61; 436/525, 526, 165; 366/117

[56] References Cited

U.S. PATENT DOCUMENTS

| 4,299,795 | 11/1981 | Bates | 422/102 X |
| 4,320,087 | 8/1982 | Chau et al. | 422/102 X |
| 4,325,910 | 4/1982 | Jordan | 422/64 |
| 4,332,906 | 6/1982 | Taylor | 422/102 X |
| 4,681,742 | 7/1987 | Johnson et al. | 422/102 |
| 4,720,374 | 1/1988 | Kamachandran | 422/102 X |

Primary Examiner—Lynn Kummert
Attorney, Agent, or Firm—Finnegan, Henderson, Farabow, Garrett and Dunner

[57] ABSTRACT

In the reaction vessel in the form of a cell for optical investigations of small quantities of liquid, the floor (4) of the reaction vessel exhibits a circular depression (6), in which a cylindrical body (9) is disposed so as to be moveable. The depression (6) exhibits arcuately extending channels (7), which extend from the depression (6) towards the walls (3) and/or the corners (8) of the reaction vessel.

1 Claim, 1 Drawing Sheet

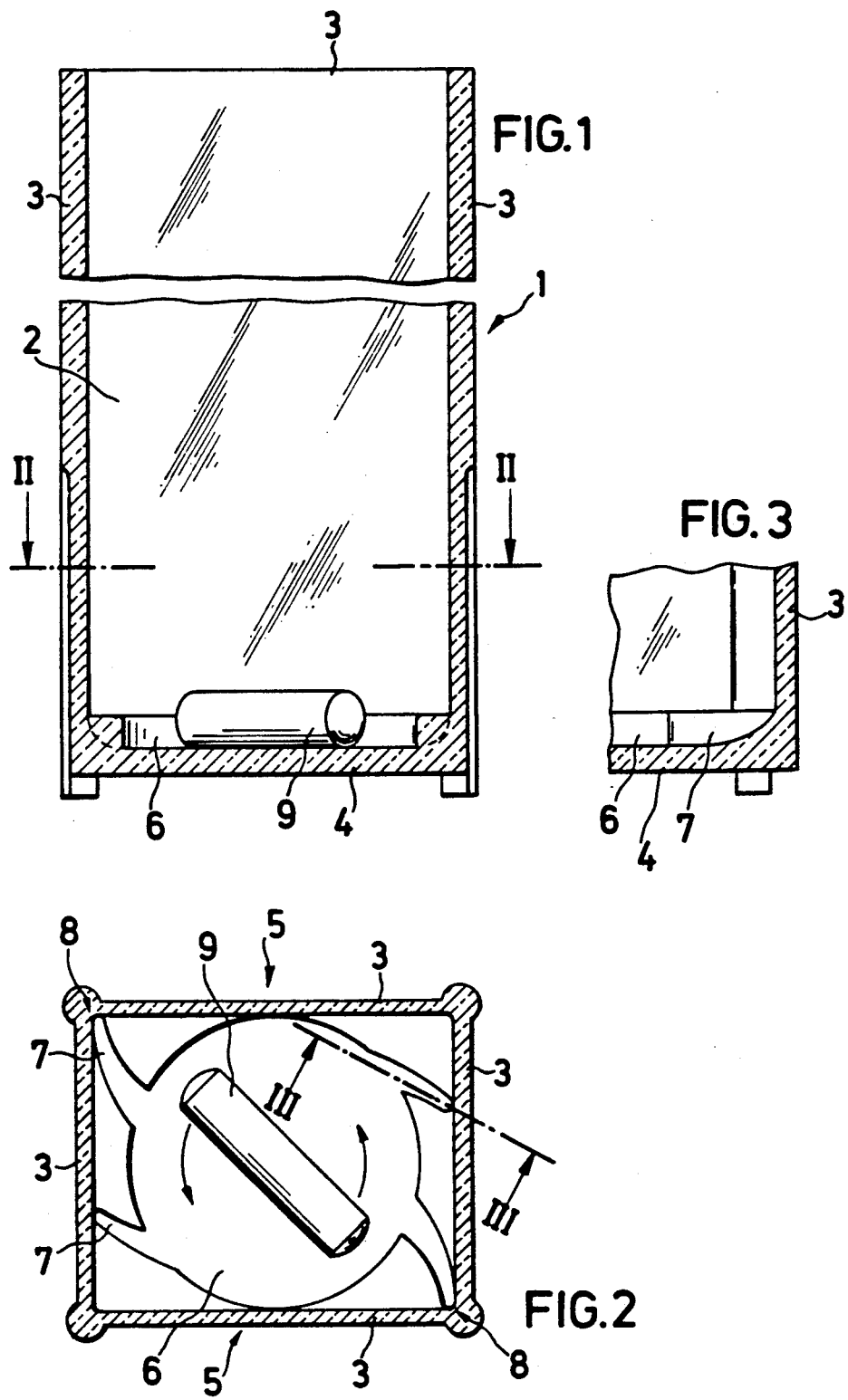

REACTION VESSEL

The invention relates to a reaction vessel in the form of a cell having parallelepipedic cavity for optical investigations of small quantities of liquid.

In the case of rapid chemical reactions, such as, for example, antigen-antibody reactions for diagnostic purposes, the quantitative result of the reaction frequently depends upon the rapid mixing of the reactants. The object is accordingly to provide a reaction vessel with which a rapid mixing of the reactants can be implemented.

The object is achieved by a reaction vessel in which the floor exhibits a circular depression, in which a cylindrical body is disposed so as to be moveable, and arcuately extending channels, which extend from the depression towards the walls and/or the corners of the reaction vessel.

The invention is explained in greater detail in the text which follows, with reference to drawings which merely represent an embodiment. In the drawings:

FIG. 1 shows the reaction vessel sectioned in side elevation,

FIG. 2 shows the cross-section II—II of FIG. 1, and

FIG. 3 shows the cross-section III—III of FIG. 2.

The reaction vessel 1 in the form of a cell having a parallelepipedic cavity 2 consists of four walls 3 and a floor 4, and two of the four walls exhibit optical windows 5 which are situated opposite one another and which stand parallel to one another. The floor 4 is provided with a circular depression 6, in which a narrow cylindrical body 9, preferably of ferromagnetic material, is disposed so as to be in a lying position and moveable.

The length of the body 9 is smaller than the diameter of the circular depression, and its diameter is at most twice as great as the depth of the depression 6. Furthermore, the floor 4 exhibits arcuately extending channels 7, which extend from the depression 6 towards the walls 3 and/or the corners 8 of the reaction vessel.

By means of the rotating cylinder 9, i.e. by means of the stirrer, liquid is drawn from the edge region into the center of the reaction vessel. By this means, the mixing is likewise accelerated.

We claim:

1. A reaction vessel for optical investigations, comprising:
   a floor;
   sidewalls extending upwardly from said floor to define a cell;
   a circular depression formed in said floor;
   a cylindrical body rotatably mounted in said circular depression for mixing reactants disposed in the vessel;
   a plurality of arcuate channels formed in said floor and extending from the periphery of said circular depression toward said sidewalls.

* * * * *